(12) United States Patent
Hermann et al.

(10) Patent No.: US 7,505,555 B2
(45) Date of Patent: Mar. 17, 2009

(54) PADS FOR MAMMOGRAPHY AND METHODS FOR MAKING AND USING THEM

(75) Inventors: George D. Hermann, Portola Valley, CA (US); Gail S. Lebovic, Frisco, TX (US)

(73) Assignee: BioLucent, LLC, Bedford, MA (US)

( * ) Notice: Subject to any disclaimer, the term of this patent is extended or adjusted under 35 U.S.C. 154(b) by 0 days.

(21) Appl. No.: 11/265,713

(22) Filed: Nov. 1, 2005

(65) Prior Publication Data
US 2006/0126794 A1    Jun. 15, 2006

Related U.S. Application Data

(60) Provisional application No. 60/624,683, filed on Nov. 2, 2004.

(51) Int. Cl.
*A61B 6/04* (2006.01)
(52) U.S. Cl. .................................... 378/37; 378/210
(58) Field of Classification Search .................. 378/37, 378/210
See application file for complete search history.

(56) References Cited

U.S. PATENT DOCUMENTS

| | | | |
|---|---|---|---|
| 3,491,753 A * | 1/1970 | Milton et al. ................. | 602/46 |
| 3,668,394 A | 6/1972 | Panzer | |
| 3,963,933 A | 6/1976 | Henkes, Jr. | |
| 3,971,950 A * | 7/1976 | Evans et al. .................... | 378/37 |
| 4,030,719 A | 6/1977 | Gabriele et al. | |
| 4,346,298 A | 8/1982 | Dixit | |
| 4,433,690 A | 2/1984 | Green | |
| 4,691,333 A | 9/1987 | Gabriele | |
| 4,923,187 A | 5/1990 | Monbrinie | |
| 4,943,986 A | 7/1990 | Barbarisi | |
| 5,044,008 A | 8/1991 | Jackson | |

(Continued)

FOREIGN PATENT DOCUMENTS

DE    23 35 576 A1    1/1975

(Continued)

OTHER PUBLICATIONS

Thomas, Martin (GLS), Ultra Softness & Wtaer Clarity Featured in New GLS Versaflex TPE Upgrade, (Sep. 18, 2002) GLS Corporation, pp. 1-2.*

(Continued)

*Primary Examiner*—Edward J Glick
*Assistant Examiner*—Anastasia Midkiff
(74) *Attorney, Agent, or Firm*—William A. English; Vista IP Law Group LLP

(57) ABSTRACT

A compression device includes a frame mountable to a mammography unit that includes a window disposed within an x-ray field of the mammography unit when the frame is mounted to the mammography unit, and a radiolucent compressible member connectable to the frame across the window for providing a compression surface within the x-ray field. For example, the compressible member may include a rigid backing member and a radiolucent pad, e.g., a gel pad, on the backing member. The backing member and frame may include tongue and groove or other connectors for connecting the compressible member to the frame. Optionally, one or more thin, radiolucent films may be removable from the compressible member, e.g., after obtaining x-rays from successive individual patients.

46 Claims, 10 Drawing Sheets

U.S. PATENT DOCUMENTS

| | | | |
|---|---|---|---|
| 5,081,657 A | | 1/1992 | Klawitter |
| 5,161,273 A | | 11/1992 | Deck |
| 5,166,968 A | | 11/1992 | Morse |
| 5,185,776 A | | 2/1993 | Townsend |
| 5,189,686 A | | 2/1993 | Hixson, Sr. |
| 5,199,056 A | * | 3/1993 | Darrah .................. 378/37 |
| 5,226,070 A | | 7/1993 | Ariba |
| 5,236,363 A | * | 8/1993 | Sandrik et al. ............. 434/267 |
| 5,377,254 A | * | 12/1994 | Walling .................. 378/167 |
| 5,398,272 A | | 3/1995 | Bouscary |
| 5,416,822 A | | 5/1995 | Kunik |
| 5,474,072 A | | 12/1995 | Shmulewitz |
| 5,479,927 A | | 1/1996 | Shmulewitz |
| 5,541,972 A | | 7/1996 | Anthony |
| 5,553,111 A | | 9/1996 | Moore |
| 5,613,254 A | | 3/1997 | Clayman |
| 5,632,275 A | | 5/1997 | Browne |
| 5,657,367 A | | 8/1997 | Couch |
| 5,664,573 A | | 9/1997 | Shmulewitz |
| 5,719,916 A | | 2/1998 | Nelson |
| 5,754,997 A | | 5/1998 | Lussi |
| 5,832,550 A | | 11/1998 | Hauger |
| 5,891,074 A | | 4/1999 | Cesurczyk |
| 5,970,119 A | | 10/1999 | Hofmann |
| 6,049,583 A | | 4/2000 | Galkin |
| 6,577,702 B1 | * | 6/2003 | Lebovic et al. ............. 378/37 |
| 2003/0007597 A1 | * | 1/2003 | Higgins et al. ............. 378/37 |
| 2003/0099325 A1 | * | 5/2003 | Galkin .................. 378/37 |
| 2004/0156472 A1 | * | 8/2004 | Galkin .................. 378/37 |

FOREIGN PATENT DOCUMENTS

| | | | |
|---|---|---|---|
| DE | 4324508 A1 | | 1/1995 |
| DE | 19926 446 A1 | | 1/2000 |
| DE | 19921 100 A1 | | 3/2000 |
| DE | 19901724 A1 | | 7/2000 |
| EP | 0 682 913 A1 | | 11/1995 |
| FR | 2 702 059 A1 | | 9/1994 |
| FR | 2853520 A1 | | 10/2004 |
| GB | 938410 | | 6/1962 |
| GB | 2049758 A | * | 12/1980 |
| WO | WO 96/07353 | | 3/1996 |
| WO | WO 96/13211 | | 5/1996 |

OTHER PUBLICATIONS

A. R. Custom Medical Products, Ltd., Custom Compression Paddles, www.arcustommedical.com/Paddle_Info.asp, Date printed: Oct. 4, 2006.

RadiologyInfo (tm), Image Gallery, Mammography, www.x-rayinfo.com/en/photocat/photos_pc.cfm!Image=mammo-machine.jpg&&pg+mammo&bhcp=1, Date printed: Oct. 4, 2006.

Bassett, Lawrence W. and Shirley Axelrod, A Modification of the Craniocaudal View in Mammography, Radiology, Jul. 1979, pp. 222-224, vol. 132 No. 1, The Radiological Society of North America.

B. Galkin, The Breast Pillow TM: A Novel Device to Reduce Patient Discomfort and Pain During Mammography . . . , http://www.aapm.org/meeting/01am/prabs.asp!mid=6&aid=7295.

The International Search Reports for PCT/US01/07189 (dated Sep. 17, 2001) and PCT/US02/23576 (dated Mar. 14, 2003).

S&S Par Scientific, VacFix Literature, HP002/0307, Houston, TX.

John K. McCulloch, Letter dated Dec. 7, 2005 with exhibits including tray liner, positioning aid literature, and 510(k) excerpt, 9 pages.

John K. McCulloch, Letter dated Dec. 9, 2005 with drawings of CFI Mammography Wedge, 3 pages.

Excerpts from Biolucent, Inc. 510(k) Notification including predicate device marketing literature, Dec. 6, 2000, 7 pages.

AAPM Report No. 29, Equipment Requirements and Quality Control for Mammography, Aug. 1990, 29 pages, For American Association of Physicists in Medicine.

Khalkhali, Iraj, Ismael Mena & Linda Diggles, Review of imaging techniques for the diagnosis of breast cancer . . . , European Journal of Nuclear Medicine, Apr. 1994, V.21, No. 4.

Cone Instruments web catalog page, Scintimammography Pad with 8 mil Vinyl Cover, Item No. NO33008, 2004 Cone Instruments, Inc.

Nuclear Medicine Instruments & Accessories catalog 28, Pinestar Technology Inc., Scintimammography Pad Set, p. 85, www.pinestar.com.

Contour Fabricators. Inc. Medical Solutions Catalog, pp. 1-25, 34, www.cfimedical.com, 2006.

Muntz, E. Phillip & Wende Westinghouse Logan, Focal Spot Size and Scatter Suppression . . . , AJR, Sep. 1979, vol. 133:453-459, American Roentgen Ray Society.

ARRT 2005 Annual Report to Registered Technologists, 64 pages, The American Registry of Radiologic Technologists, St. Paul, Minnesota.

Wochos, John F., Gary D. Fullerton, & Larry A. DeWerd, Mailed Thermoluminescent Dosimeter Determination of Entrance Skin . . . , Am J Roentgenol 131:617-19, Oct. 1978.

Pagani, John J., Lawrence W. Bassett, et al., Efficacy of Combined Film-Screen/ Xeromammography, AJR, Jul. 1980, vol. 135:141-6, American Roentgen Ray Society.

Parekh, N. J. & John N. Wolfe, Localization Device for Occult Breast Lesions . . . , AJR, Apr. 1987, vol. 148:699-701, American Roentgen Ray Society.

Wolfe, John N., Xeroradiography of the Breast, Second Edition, 1974, pp. 22 & 660, Charles C. Thomas publisher, Springfield, Illinois, USA.

Robert L. Egan, M.D., Technologist Guide to Mammography, Second Edition, 1977, pp. 42-3, 93-4 & 97, The Williams & Wilkins Company, Baltimore, Maryland.

Lawrence Bigongiari, M.D., Barbara Threatt, et al., Dependent Compression Mammography, The Journal of Kansas Medical Society, Jun. 1979, vol. 80:336-40, Kansas City, Kansas.

Lawrence Bigongiari, M.D., Barbara Threatt, et al., A Simple Device for Dependent Compression Mammography, Radiology, Aug. 1977, 124:516-17, Univ. of MI, Ann Arbor, Michigan.

Howard Sochurek, Medicine's New Vision, 1988, p. 114, Mack Publishing Company, Easton, Pennsylvania.

Daniel B. Kopans, M.D., Chapter 5: Mammography, Breast Imaging, 1989, pp. 34-59, J.B. Lippincott Company, Philadelphia.

GE Medical Systems, GE Accessories and Supplies for Diagnostic Imaging, Catalogue pages, Copyright 1995, vol. 5, General Electric, Milwaukee, Wisconsin.

GE Medical Systems, GE Accessories and Supplies for Diagnostic Imaging, Catalogue pages, Copyright 1997, vol. 6, General Electric, Milwaukee, Wisconsin.

GE Medical Systems, GE Accessories, Catalogue pages, 1997/98, Copyright 1997, General Electric, Milwaukee, Wisconsin, printed in France, 1997.

* cited by examiner

PADS FOR MAMMOGRAPHY AND METHODS FOR MAKING AND USING THEM

The present application claims benefit of application Ser. No. 60/624,683, filed Nov. 2, 2004, the entire disclosure of which is expressly incorporated by reference herein.

FIELD OF THE INVENTION

The present invention relates generally to compression devices for mammography or other x-ray procedures and methods for using such compression devices, and more particularly to devices and methods for cushioning or padding surfaces of compression plates applied to body parts during x-ray procedures, for example, during mammography, biopsies, and the like.

BACKGROUND

During mammography, a patient's breast is placed under compression by opposing plates attached to a mammography unit. Once under compression, an x-ray may be taken to determine the presence or absence of suspect lesions in the breast tissue, e.g., calcifications or tumors. An important reason for compressing the breast during mammography is to provide a thinner cross-section of tissue for the x-rays to pass through. When the breast is compressed, it may provide optimal imaging of tissue abnormalities and/or may allow lower doses of x-ray radiation to be used, thereby reducing x-ray radiation exposure to the patient.

FIGS. 1, 2A, and 2B show a mammography unit 10, including a base 12 and a rotating assembly 14 that includes an x-ray source 16, a compression paddle 18, and an x-ray plate 20. The x-ray plate 20, often referred to as a "bucky," is stationary relative to the assembly 14, while the compression paddle 18 may be attached to an interchange assembly 22 that is movable relative to the x-ray plate 20.

As best seen in FIG. 2A, the x-ray plate 20 generally includes two patient contact surfaces, a primary tissue contact surface 24 and a front surface 26, as well as side surfaces 28. At least one of the side surfaces 28 may include an opening 30 into which an x-ray cassette 32 may be inserted. As best seen in FIG. 2B, the compression paddle 18 also generally includes two patient contact surfaces, a primary tissue contact surface 34 and a front surface 36, as well as two side surfaces 38. Additional configurations of compression plates and accessories that may have various shapes and sizes depending upon a patient's anatomy and/or the type of x-ray view are shown in U.S. Pat. Nos. 6,577,702 and 6,765,984, the entire disclosures of which are expressly incorporated by reference herein.

With the patient (not shown) leaning against the front surfaces 26, 36, the patient's breast (also not shown) is placed on the primary contact surface 24 of the x-ray plate 20 and the compression paddle 18 is moved towards the x-ray plate 20 to compress the breast between the primary contact surfaces 24, 34. A series of x-rays may be taken of the breast tissue, e.g., which may involve moving the assembly 14 and/or repositioning the patient's breast after one or more film exposures.

One of the problems with mammography is that the patient may experience significant discomfort during compression of the breast. Because of this, some women may avoid having a mammogram taken rather than experience the pain that may be caused during the procedure. Although patients may tolerate the pain caused by compression up to about ten to eleven (10-11) compression units, clinical mammography may involve up to sixteen to eighteen (16-18) compression units. If greater compression is used, the quality of the mammogram may be enhanced, thereby increasing the physician's ability to detect cancers or suspect lesions. However, with greater compression comes increased discomfort.

U.S. Pat. No. 5,541,972, issued to Anthony, discloses a padding device that may be added to cover the front surface of an x-ray plate. Because the padding device is made from materials that may be radiopaque, the padding device is generally positioned to avoid disposing it within the field of the x-ray plate.

U.S. Pat. No. 5,185,776, issued to Townsend, discloses a radiolucent pad that is glued to a sleeve. An x-ray cassette may be inserted into the sleeve, a patient may be disposed against the pad, and an x-ray image obtained. The sleeve and pad are disposed of after the x-ray procedure. Disposing of the entire x-ray sleeve after a single use, however, may increase the cost of x-ray procedures.

Accordingly, devices and methods for cushioning compression surfaces, e.g., during mammography, would be useful.

SUMMARY OF THE INVENTION

The present invention is directed to compression or cushioning devices and/or methods for cushioning surfaces, for example, for cushioning or padding surfaces of compression devices contacting body parts during x-ray procedures, such as during mammography, biopsies, and the like. More particularly, the present invention is directed to cushioning devices including gel or other radiolucent compressible materials, to multiple component compression devices, e.g., including reusable components and disposable components, and/or to methods for making or using such devices.

In accordance with one embodiment, a cushioning device is provided for a compression plate that includes a substantially rigid base including a first surface, and a radiolucent gel pad on at least the first surface. The base may be coextensive with the gel pad or may provided a border for supporting the gel pad. Optionally, the base may include one or more additional surfaces that extend substantially transversely relative to the first surface and the gel pad may cover at least a portion of the one or more additional surfaces. In one embodiment, the base may be connectable to a compression plate and/or an x-ray device such that the first surface is disposed within an x-ray field of the x-ray device.

In accordance with another embodiment, an apparatus for an x-ray device is provided, that includes a frame mountable to the x-ray device that includes a window disposed within an x-ray field of the x-ray device, and a radiolucent compressible member connectable to the frame across the window for providing a compression surface within the x-ray field.

In one embodiment, the apparatus may include a semi-reusable and/or a disposable portion including a substantially rigid base including a first surface and a radiolucent cushioning element on the first surface. Optionally, one or more removable films may be provided on the first surface that may be removed after use. In addition or alternatively, the base may include one or more additional surfaces and the cushioning element may be provided on the one or more additional surfaces.

In addition, the apparatus may include a reusable frame or other device to which the base may be connected. For example, the frame may include at least a portion of a compression device, e.g., a compression paddle or bucky, that includes a window across which the base may be secured. The base and/or frame may include one or more connectors, e.g., mating tongues and grooves, that facilitate removably securing the base to the frame.

In accordance with still another embodiment, a cushioning device is provided for a mammography unit that includes a radiolucent gel pad including a first surface and a second surface, and means for removably attaching the pad to a compression surface on the first surface. In an exemplary embodiment, the pad is substantially transparent and/or the means for removably attaching the pad includes an adhesive.

In accordance with yet another embodiment, a method is provided for performing mammography that includes providing a mammography paddle connected to a mammography unit, the mammography paddle including a substantially transparent cushioning element on a patient contact surface of the mammography paddle. A breast is compressed using the mammography paddle, the breast is visually monitored through the cushioning element during positioning, and a mammogram is obtained of the compressed breast.

In one embodiment, a frame is connected to the mammography unit, the frame including an opening extending across an x-ray field of the mammography unit, and a substantially transparent pad device is connected to the frame such that the pad device extends across the opening.

Optionally, e.g., in the automatic exposure setting mode of the mammography machine, x-rays may be emitted through the mammography paddle, and a dosage of x-rays emitted when the mammogram is obtained may be adjusted to account for attenuation of the gel pad.

In accordance with another embodiment, a method is provided for performing mammography using a mammography unit including a compression plate, the compression plate including an opening within an x-ray field of the mammography unit. A radiolucent cushioning element may be connected to the compression plate across the window, a breast may be compressed using the cushioning element, the cushioning element deforming under forces applied during compression to provide comfort, and a mammogram may be obtained of the compressed breast.

Other aspects and features of the present invention will become apparent from consideration of the following description taken in conjunction with the accompanying drawings.

DETAILED DESCRIPTION OF THE PREFERRED EMBODIMENTS

Figure 1:
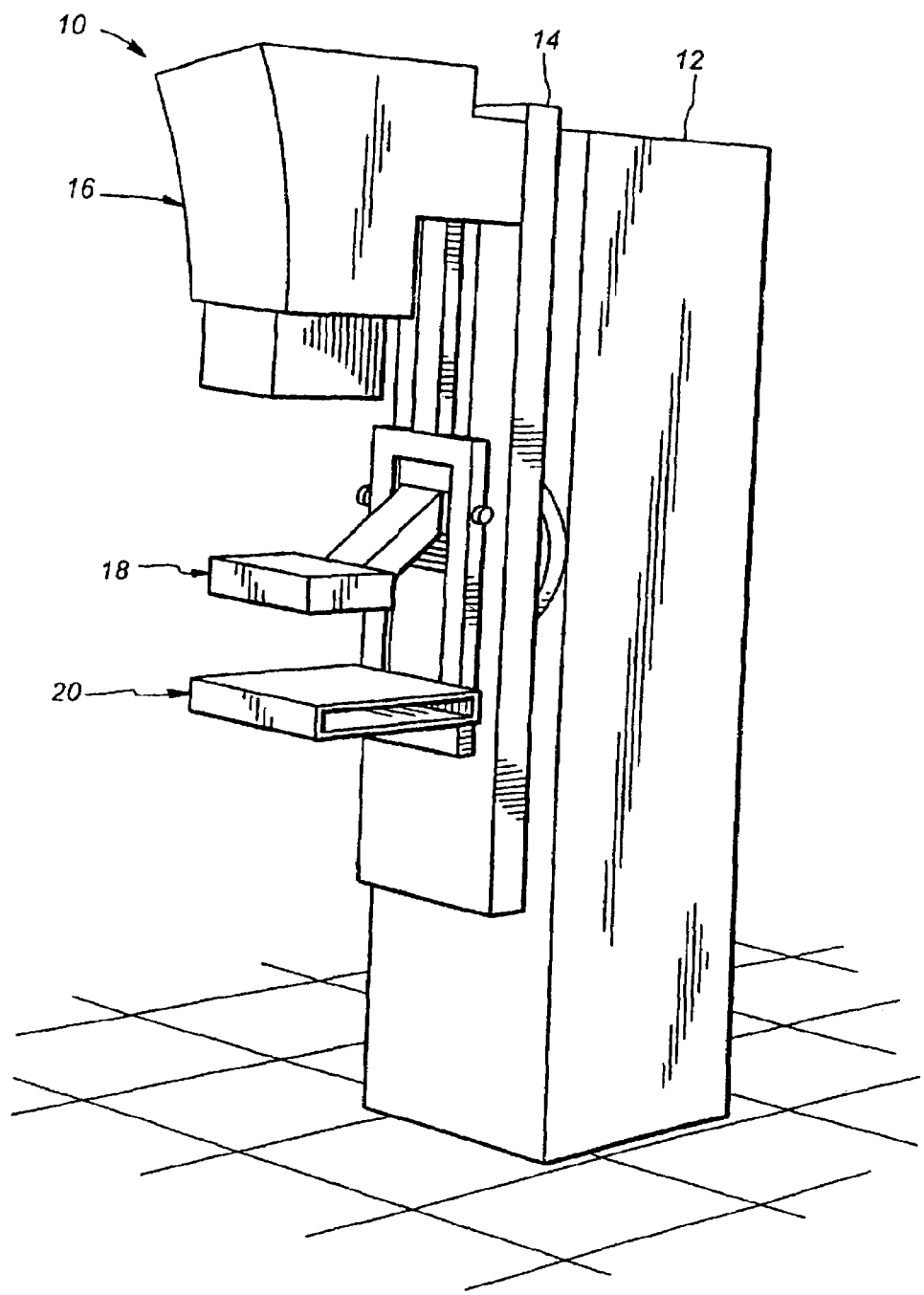
FIG. 1 is a perspective view of a mammography unit, including a compression paddle and an x-ray plate.
Figure 2A:
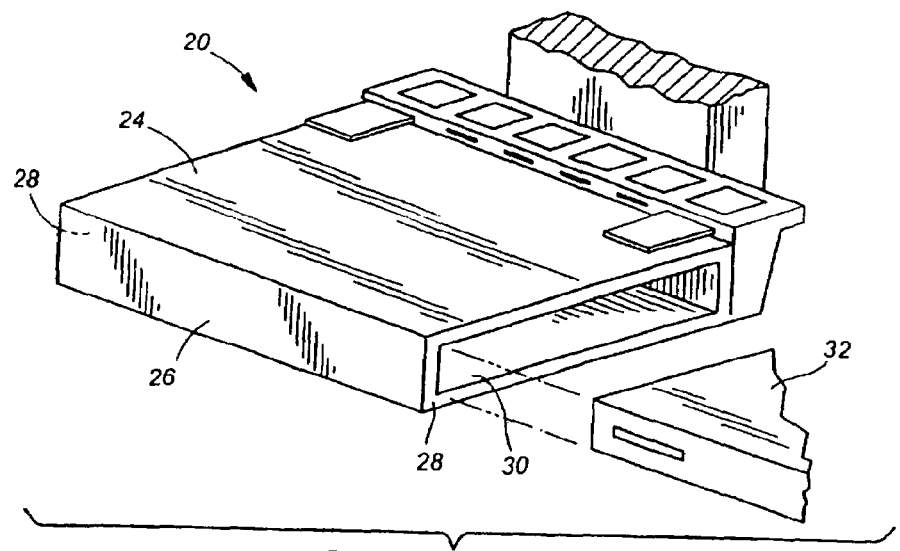
FIG. 2A is a perspective view of the x-ray plate or "bucky" of FIG. 1.
Figure 2B:
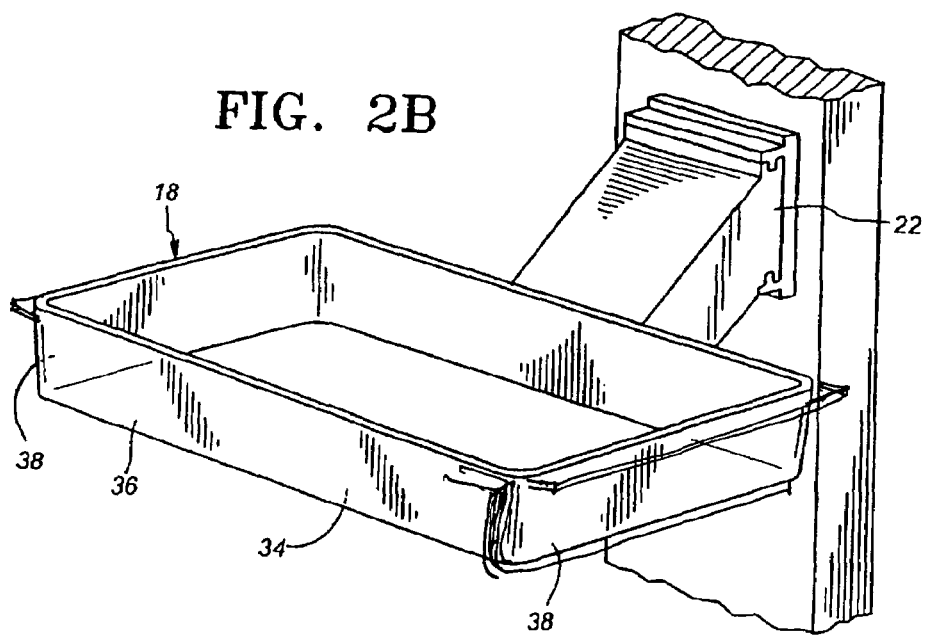
FIG. 2B is a perspective view of the compression paddle of FIG. 1.

Turning to FIGS. 3-6, an exemplary embodiment of a device 100 is shown for cushioning a compression surface of an x-ray device, such as the mammography unit 10 of FIG. 1. In the configuration shown, the cushioning device 100 may be mounted or otherwise placed on or over an x-ray plate, such as the bucky 20 shown in FIG. 2A. It will be appreciated that the cushioning device 100 may be used in conjunction with other compression devices (not shown).

Generally, the cushioning device 100 includes a frame 110 that may be mounted on or adjacent a compression device (not shown) and a pad device 120 that may be connected to the frame 110. Optionally, one or more disposable covers 130 may be provided on the pad device 120, as described further below. In the exemplary embodiment shown in FIG. 3, the frame 110 may include a back panel 112, and opposing side panels 114 extending from opposite ends of the back panel 112 to define a window or opening 116 therebetween.

Figure 3:
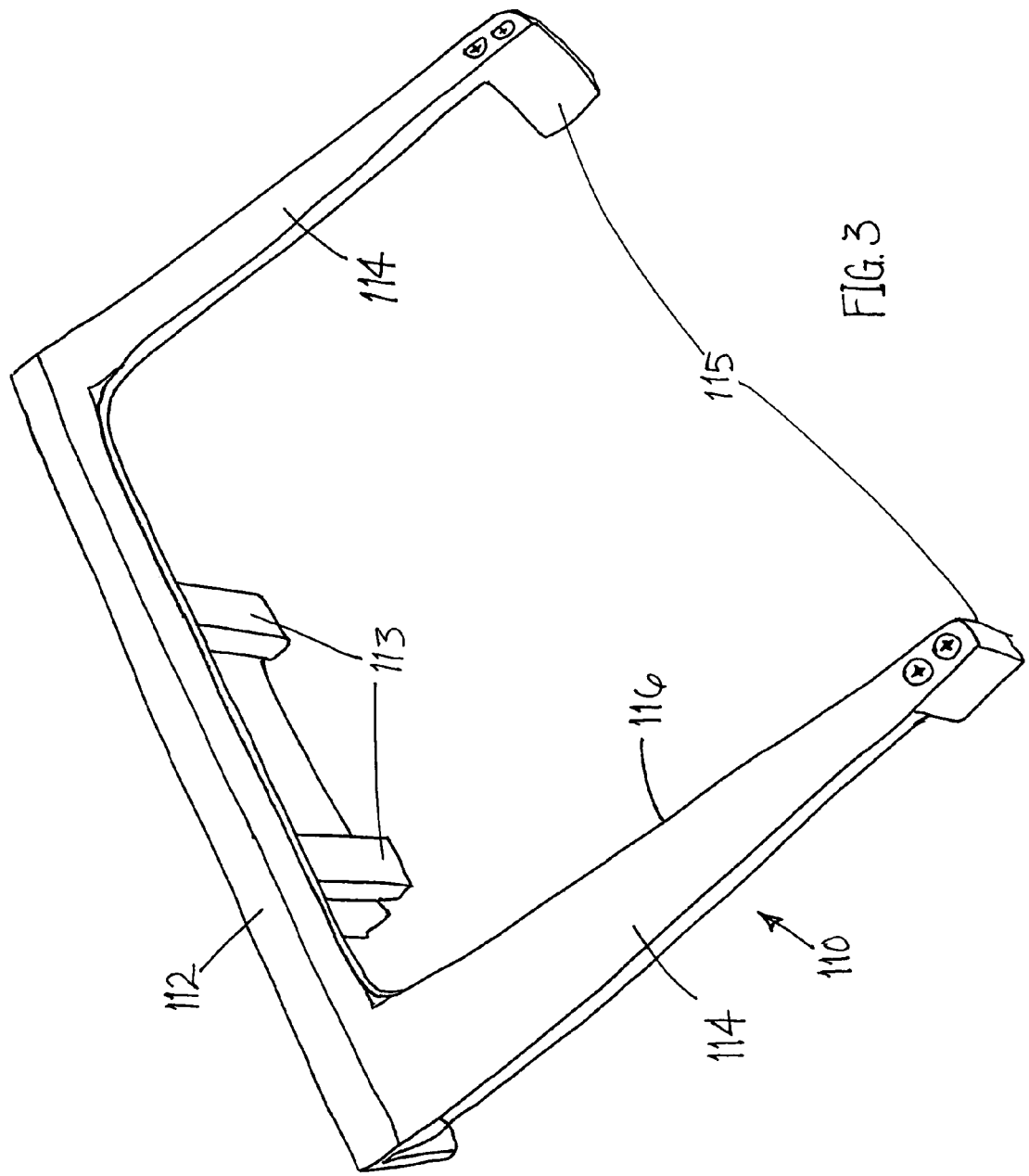
FIG. 3 is a perspective view of a frame that may be mounted to a mammography unit, which, when combined with a compression element, can serve as a compression paddle similar to that shown in FIG. 2B.

The frame 110 and/or compression device may include one or more connectors for removably or permanently attaching the frame 110 to the compression device. As shown in FIG. 3, for example, the frame 110 may include feet or other elements 113, 115 that extend from the back and/or side panels 112, 114. The feet 113, 115 may slidably engage one or more surfaces of the compression device, e.g., to stabilize, secure, and/or connect the frame 110. For example, with additional reference to FIG. 2A, the compression device may be an x-ray plate or bucky 20, and the front feet 115 may engage side surfaces 28 of the bucky 20 while the back feet 113 engage the back surface (not shown) of the bucky 20, thereby securing the frame 110 relative to the bucky 20.

Alternatively, a portion of the frame 110, e.g., the back side of feet 113, may include one or more mounts or other connectors (not shown) for attaching the frame 110 directly to a mammography unit (not shown), similar to the connectors used on conventional compression plates. The frame 110 may be formed from plastic, metal, or composite materials, e.g., by injection molding, casting, machining, and the like, as a single component or as multiple components that are assembled together.

Returning to FIG. 3, when the frame 110 is mounted to; placed on, and/or secured to a compression device (not shown), the window 116 may overlie a primary compression surface of the compression device, e.g., which may lie in the x-ray field of the x-ray unit (also not shown). For example, with additional reference again to FIG. 2A, the frame 110 may be mounted to and/or over the bucky 20 such that the window 116 overlies primary contact surface 24. Optionally, the side panels 114 of the frame 110 may be bent or otherwise extend transversely at the front such that the side panels 114 extend along opposing edges of the front surface 26 of the bucky 20 (not shown).

Figure 4:
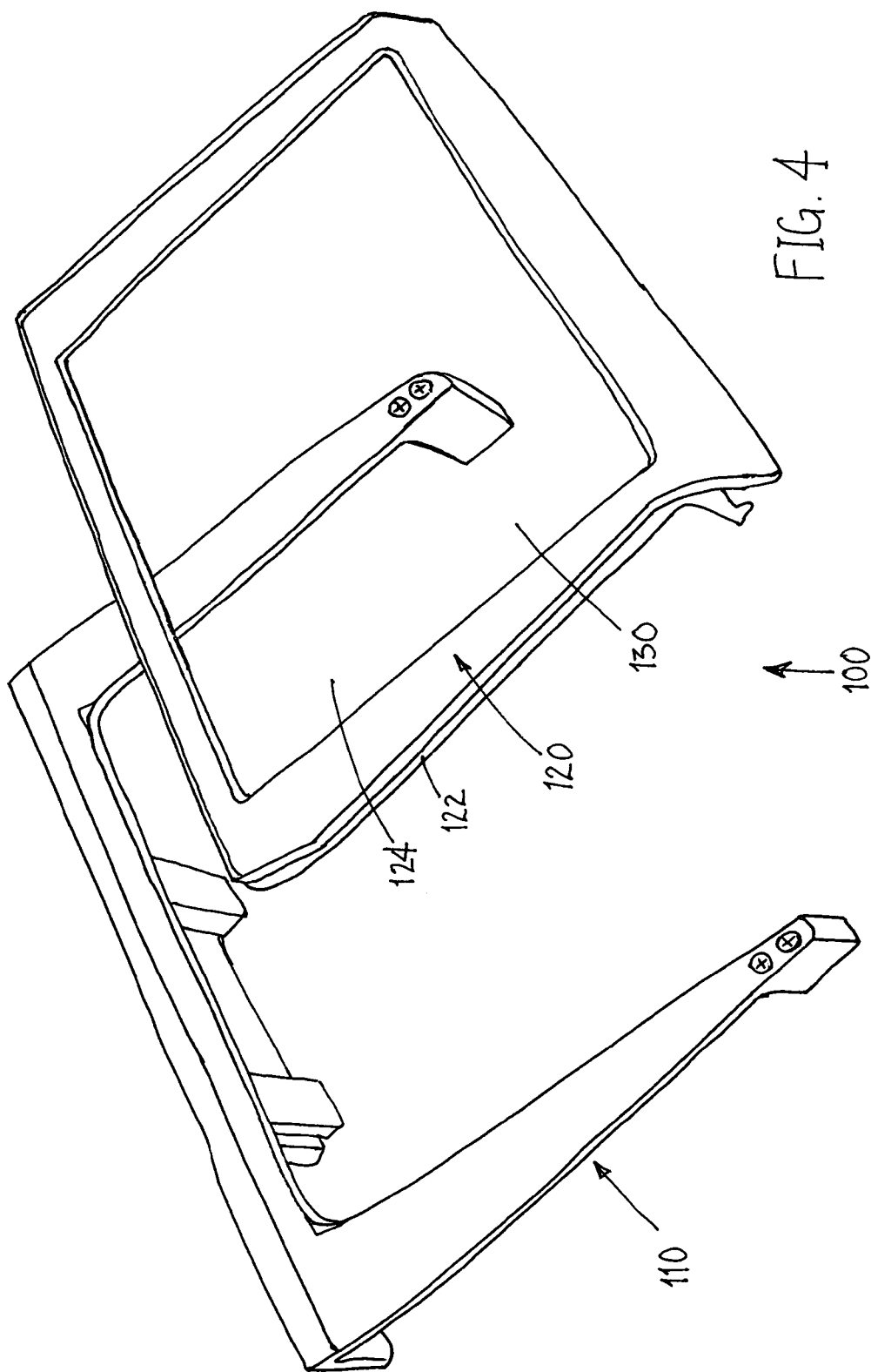
FIG. 4 is a perspective view of the frame of FIG. 3 and a cushioning element.

Turning to FIG. 4, the pad device 120 may include a backing member 122 and a pad 124. The backing member 122 may provide a substantially rigid substrate or base that may at least partially support the pad 124. As shown, the backing member 122 extends around an outer edge or periphery of the pad 124, i.e., thereby defining an opening over which the pad 124 lies. Alternatively, the backing member 122 may be a continuous sheet or panel beneath the pad 124, i.e., without the opening.

The backing member 122 may be securable to the frame 110, e.g., substantially permanently or removably attached to the frame 110. The backing member 122 may be securable to the frame 110 by cooperating detents or other connectors (not shown), an interference fit, chemical bonding, mechanical bonding, sonic welding, and the like. For example, similar to other embodiments described below, the side panels 114 of the frame 110 may include horizontal slots (not shown) and the backing member 122 may include tabs (also not shown) or simply side edges that may be slidably inserted into the slots, allowing the backing member 122 to be removably secured to the frame 110. Alternatively or in addition, hook and loop connectors, cooperating snaps, and/or posts and slots (not shown) may be used, similar to other embodiments described herein.

The backing member 122 may be manufactured of suitable materials, e.g., plastics such as acrylic or polycarbonate. The backing member 122 may be formed using a variety of methods, such as injection molding, heat setting, extrusion, and/or machining. It may be desirable to make the backing member 122 as thin as possible, e.g., to minimize x-ray absorption, while providing sufficient support for the pad 124 under compression. In an exemplary embodiment, the backing member 122 may have a thickness between about 2.4-6.4 mm (3/32-1/4 inch).

Any portions of the backing member 122 within the x-ray field should be "radiolucent," i.e., should produce no significant visual artifacts on a mammogram, although, optionally, all of the backing member 122 may be formed from radiolucent material to facilitate manufacturing. In addition, in some embodiments, it may be desirable to make the backing member 120 from substantially transparent material, particularly if the backing member 122 is substantially continuous, e.g., to facilitate observation through the backing material 122 and pad 124, as described further below.

Optionally, the pad 124 may include a fabric layer impregnated into one or more surfaces of the pad 124, e.g., a lower surface to provide a substrate for adherence to the perimeter of the backing member 122. Such a fabric layer may be provided only about a perimeter of the pad 124, i.e., not in the imaging area of the pad 124, to avoid impacting x-rays. Fabric may also be adhered to, impregnated in, or otherwise provided on the side panels 114 to increase comfort, e.g., when the exposed surfaces are contacted by a patient's skin.

Figure 5:
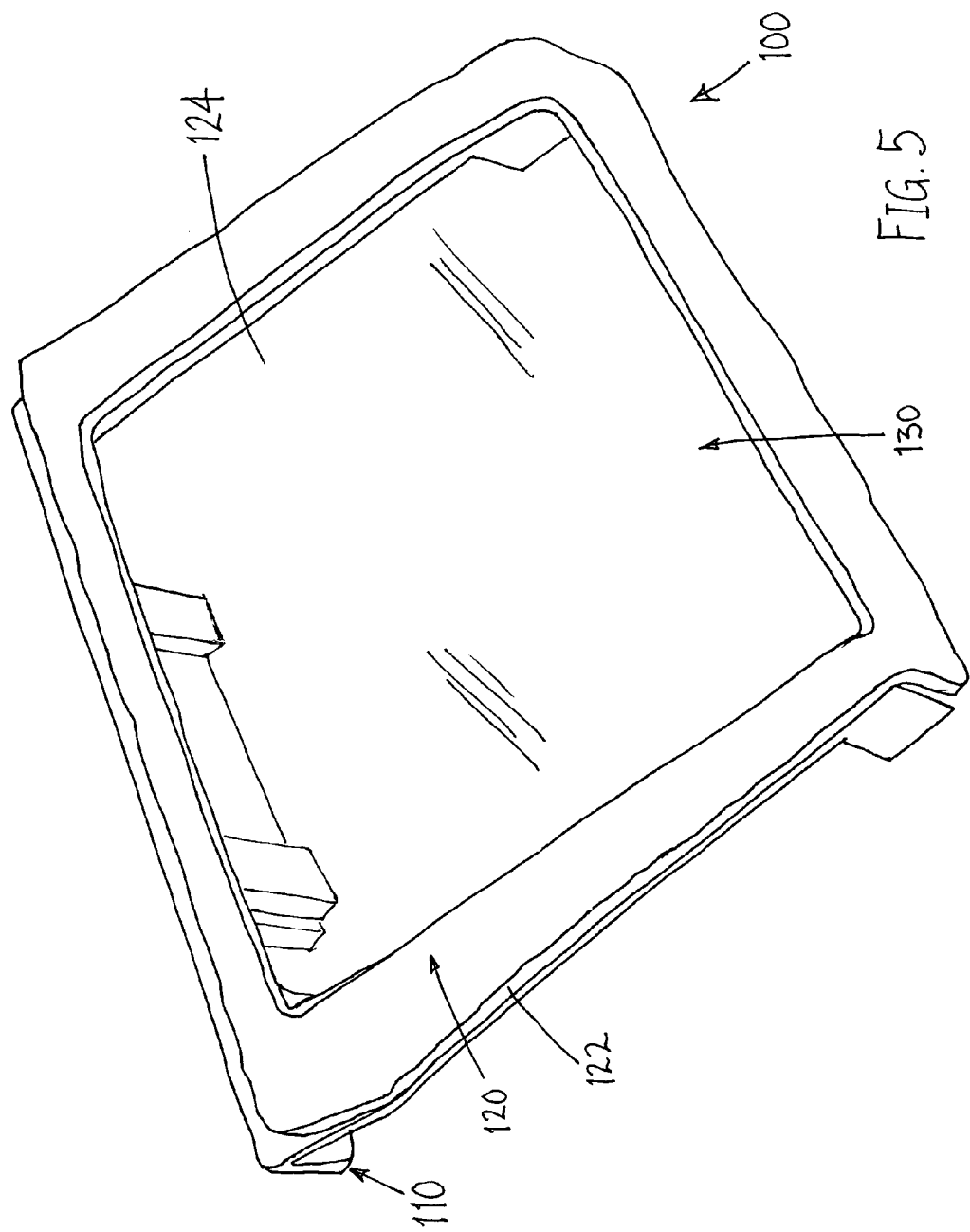
FIG. 5 is a perspective view of the frame of FIGS. 3 and 4 with the cushioning element secured to the frame.

With continued reference to FIGS. 4 and 5, the pad 124 may be formed from compressible, resilient material, e.g., foam, gel, and the like. Generally, the pad 124 may give somewhat when compressed, e.g., to increase comfort to a patient's breast being compressed during mammography, yet resiliently expand back to its original size and/or shape when any compressive forces are removed. In addition, the pad 124 is generally radiolucent, i.e., such that the pad 124 produces no significant visual artifacts on a mammogram or other x-ray. In one embodiment, the pad 124 may be formed from a substantially transparent and/or colorless material, which may facilitate observation of a breast or other tissue structure during a mammography or other x-ray procedure, as described further below.

In an exemplary embodiment, the pad 124 may be formed from open cell foam, such as polyurethane, neoprene, or polyolefin. The foam may have a layer of adhesive on one side, e.g., to attach the resulting pad 124 to the backing member 122. Additional information on foam pads, adhesive layers, and methods for making and using them are disclosed in U.S. Pat. Nos. 6,577,702 and 6,765,984, incorporated by reference above.

In another embodiment, the pad 124 may be formed from a gel, i.e., a colloid in which the disperse phase has combined with the dispersion medium to produce a semi-solid material. Stated differently, the gel may be a semi-solid material that is deformable under load but is substantially incompressible. Some gels, such as silicone gels, may be disfavored because of their relative radiopacity, while other gels, such as thermoplastic elastomer ("TPE") gels, may have a substantially low "z," i.e., may be substantially radiolucent. Exemplary TPE gels are available from GLS Corp. of McHenry, Ill. identified as the Versaflex® CL 2003 series of TPEs and Monprene® gels from Teknor Apex of Pawtucket R.I. Dermasol DS-300 may also be used.

The pad 124 may be substantially uniform in construction or may include multiple components. In exemplary embodiments, if the pad 124 is made from gel material, the pad 124 may have a thickness between about two and ten millimeters (0.08-0.40 inch). A thicker pad may increase compressibility and comfort, but may also increase the required dose to obtain a mammogram, as explained further below. In other embodiments, the pad 124 may include an air-filled pillow, e.g., a sealed skin containing a predetermined volume of air or other fluid therein.

The pad 124 may be attached to the backing member 122, e.g., using adhesives, fasteners (not shown), and the like. In an exemplary embodiment, the pad 124 is substantially permanently attached to the backing member 122. Alternatively, the pad 124 may be removably attached from the backing member 122.

In a further alternative embodiment, the pad 124 may be attached directly to the frame 110 and the backing member 122 may be eliminated. In this alternative, the frame 110 and the pad 124 may comprise an integral unit or the pad 124 may be removably attached to the frame 110. In still a further alternative, the pad 124 may be provided as a stand-alone device that may be attached to one or more compression surfaces of a compression device. In this alternative, the pad 124 (whether foam or gel material) may include a layer of adhesive (not shown) for removably attaching the pad 124 to the compression surface(s). Methods for attaching and using such pads are disclosed in U.S. Pat. Nos. 6,577,702 and 6,765,984, incorporated by reference above.

If the pad 124 extends around multiple surfaces, e.g., similar to the other embodiments described below, the pad 124 may be notched or have portions removed to facilitate bending the pad 124 around sharp corners. Alternatively, the edges between adjacent surfaces may be sufficiently rounded or radiused to allow the pad 124 to be wrapped or otherwise extended onto multiple surfaces.

If desired, one or more exposed surfaces of the pad 124 may include a coating, layer, or other material that changes the tackiness of the covered surface(s). Some gels may be inherently tacky, thereby providing one or more tacky contact surfaces that facilitate adherence to a compression surface but may be undesirable for patient contact. Other gels or other materials may be less tacky, such as the TPE Versaflex® gel material described above, which may be preferable for patient contact but not suitable for adhering sufficiently to a compression surface. For such materials, a film, sheet, coating, or other skin may be applied over the desired surface(s). In an exemplary embodiment, a relatively thin skin of acrylic adhesive-backed polyester or similar material, e.g., between about 0.05-0.20 millimeter (0.002-0.008 inch) thickness, may be provided to increase tackiness.

Alternatively, it may be desired to provide one or more contact surfaces that are less tacky. For such applications, the TPE Versaflex® gels described above may be appropriate. In addition or for other materials, non-tacky surface coatings may be applied to the desired contact surface(s). In an exemplary embodiment, a layer of polyurethane, e.g., between about 0.025-0.125 mm (0.001-0.005 inch) may be molded or otherwise provided over the pad 124.

Figure 6:
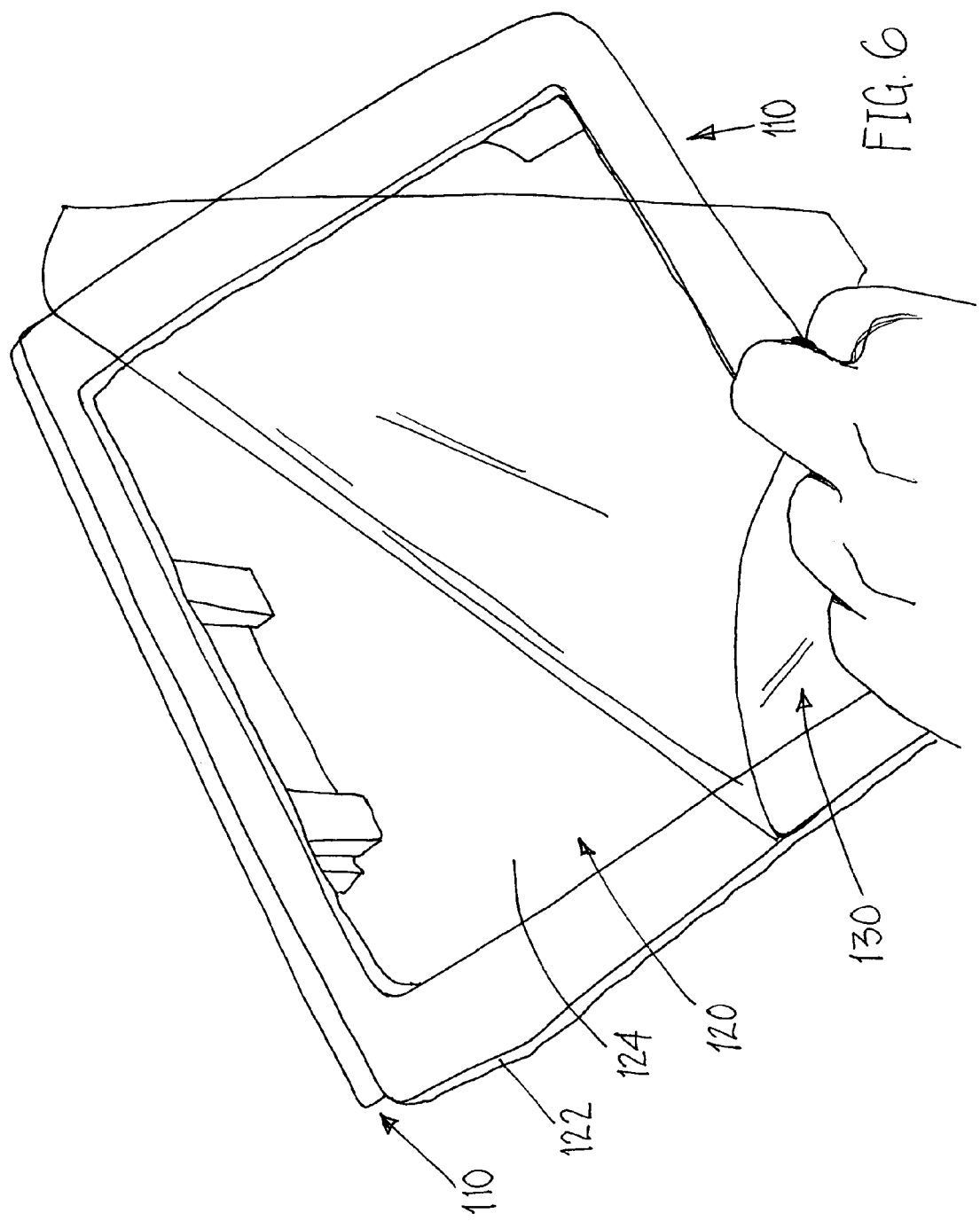
FIG. 6 is a perspective view of the frame and cushioning element of FIGS. 3-5, showing a disposable cover being removed from the cushioning element.

Turning to FIG. 6, in addition or alternatively, one or more disposable covers 130 may be provided on the pad device 120. Each cover 130 may be a relatively thin, radiolucent film that may be removably secured onto the exposed surface of the pad 124. Optionally, a plurality of covers (not shown) may be provided on top of one another that may be removable successively from the pad 124, e.g., after use on individual patients. The cover(s) 130 may be formed from film or other sheets of polyurethane, polyolefin, polyester, and the like, e.g., having a thickness of between about one and five mils (0.001-0.005 inch). The cover(s) 130 may also be substantially transparent, e.g., such that the cover(s) 130 allow tissue to monitored therethrough, e.g., if the pad 124 is also substantially transparent.

The cover(s) 130 and/or the pad 124 may be sufficiently tacky that the cover(s) 130 may be secured to the pad 124 and/or any adjacent cover(s). Alternatively, a low-tack adhesive (not shown) may be applied over one or both surfaces of each cover 130. As shown in FIG. 6 and described further below, after use, e.g., after each individual patient, a cover 130 may be removed to expose a new, clean cover (not shown) for the next patient. After all of the covers have been used, the pad device 120 may be disposed of, as described further below.

For example, during use, the frame 110 may be placed over an x-ray plate (not shown). The frame 110 may provide an interface between a conventional bucky and the pad 120. The pad device 120 may then be connected to the frame 110, as described above. A patient's breast or other tissue structure (not shown) may be positioned on the pad device 120, compressed, e.g., using a compression paddle (also not shown), and one or more x-rays may be obtained. After the procedure on the patient is complete, the pad device 120 may be replaced with another new pad device. Alternatively, if the pad device 120 includes one or more covers 130, a cover 130 may be removed, thereby providing a clean contact surface for the next patient. In this alternative, after the final cover 130 is removed, the pad device 120 may be used for an additional patient before discarding or may be discarded, and replaced with another pad device including a new set of covers.

Figure 7:
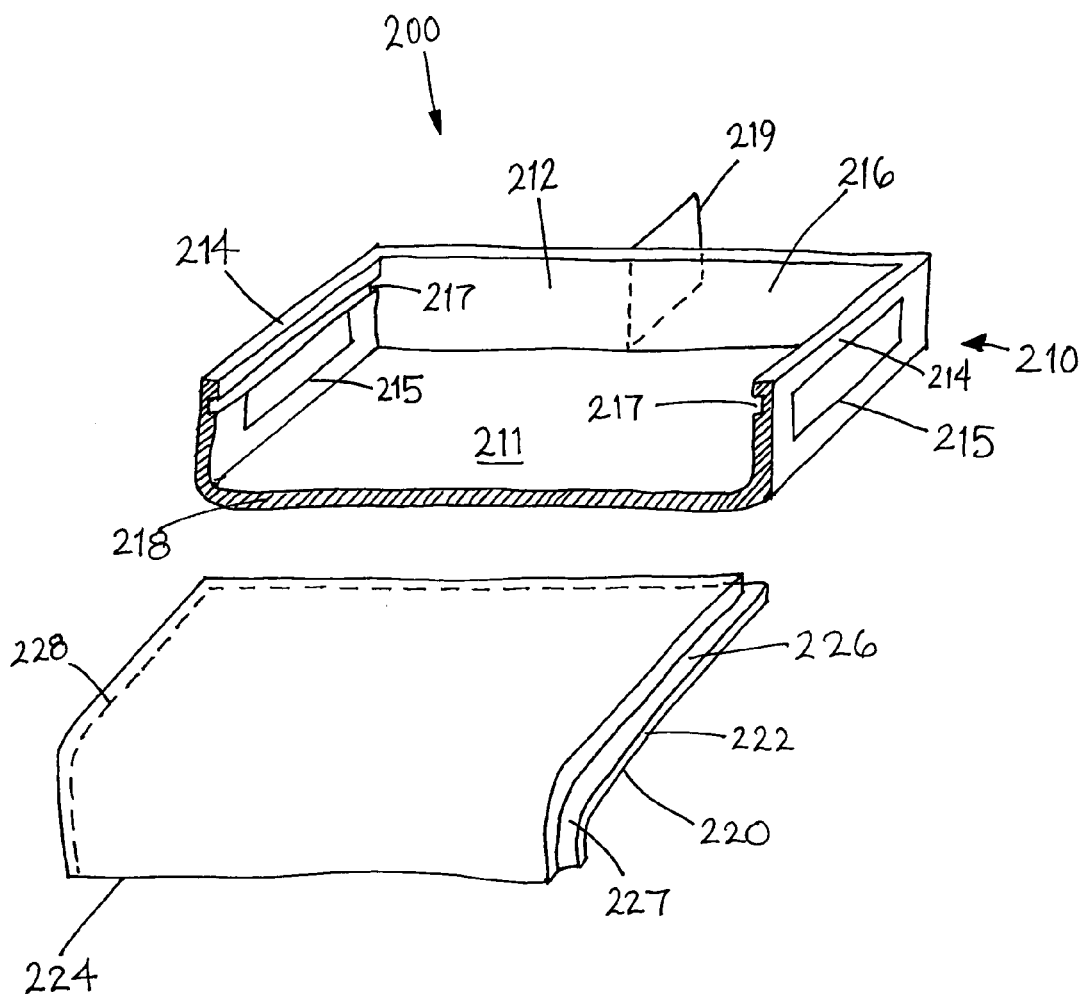
FIG. 7 is a perspective view of an embodiment of a compression device that includes a frame similar to a bucky, but including an open window in a top surface thereof, and a cushioning element connectable to the frame across the window.

Turning to FIG. 7, another embodiment of a compression device 200 is shown that includes a frame 210 and a pad device 220, which includes a backing member 222 and a pad 224. Generally, the frame 210, backing member 222, and pad 224 may be formed using similar materials and methods to the other embodiments described herein.

The frame 210 may be similar to a bucky, i.e., including a back panel 212, side panels 214, and a lower panel 218, thereby at least partially defining a cavity 211. In addition, one or both side panels 214 may include slots 215, e.g., for inserting an x-ray cassette (not shown) into the cavity 211 and/or for removing an x-ray cassette from the cavity 211. The frame 210 may include other components, such as motors, springs, and the like (not shown), for facilitating inserting and/or removing x-ray cassettes, similar to conventional bucky devices. In a further alternative, the frame 210 may be constructed similar to a bucky for a digital mammography unit, i.e., that may include an x-ray image receptor without a cavity for receiving x-ray cassettes, but with an opening therein.

In addition, the back panel 212 or other portion of the frame 210) may include a mount 219 for attaching the frame 210 to a mammography unit (not shown). The mount 219 may include one or more posts or other connectors (not shown), similar to those used to attach a conventional bucky or other compression device to a mammography unit.

Unlike a bucky, the frame 210 includes a window or opening 216 instead of an upper patient contact surface. Optionally, the window 216 may also extend to a front of the frame 210, instead of including a front surface. In addition, the frame 210 includes one or more connectors for connecting the pad device 220 to the frame 210. As shown, the side panels 214 include slots 217 for slidably receiving a portion of the pad device 220 therein to secure the pad device 220 across the window 216. Alternatively or in addition, other connectors may be provided on the frame 210, e.g., including hook and loop fasteners, cooperating detents, latches, and the like (not shown).

The backing member 222 may be formed from substantially rigid material, e.g., a sheet of plastic, such as polycarbonate and the like, to provide a substantially rigid base supporting the pad 224, similar to the backing member 122 described above. The backing member 222 may be shaped to substantially enclose the window 216 when the pad device 220 is connected to the frame 210. For example, as shown, the backing member 222 includes a first or upper surface 226 and a second or front surface 227. The second surface 227 may extend transversely relative to the first surface 226, thereby defining a generally "L" shaped cross-section. In the embodiment shown, the second surface 227 may extend substantially perpendicular to the first surface 226 with a radiused transition between the first and second surfaces 226, 227. Alternatively, the second surface 227 may be eliminated, e.g., if a front surface is provided on the frame 210 (not shown).

The backing member 220 is connectable to the frame 210, e.g., such that the first surface 226 is disposed within the x-ray field of the mammography unit. As shown, the backing member 220 includes side edges 228 that are sized to be slidably received in the slots 217 in the frame 210. In addition or alternatively, the backing member 222 may include other connectors (not shown) for securing or otherwise connecting the pad device 220 to the frame 210.

The pad 224 is a compressible radiolucent material, similar to those described elsewhere herein. The pad 224 may be substantially permanently or removably attached to the backing member 222 such that the pad extends onto the first and second surfaces 226, 227. Alternatively, separate pads may be provided on the first and second surfaces 226, 227. In a further alternative, if the frame 210 includes a front surface, a separate pad may be provided on the front surface of the frame 210 (not shown).

In a further alternative, the backing member 222 may be eliminated and the pad 224 may be attachable directly to the frame 210 across the window 216. In this alternative, an x-ray cassette (not shown) may provide an underlying support surface for the pad 224. One of the advantages of this alternative is that a thickness of material, namely the backing member 222, is reduced, which may reduce the x-ray dosage required or otherwise improve completion of a mammography procedure, as described further below. Optionally, the pad 224 may include an adhesive or otherwise have a tacky lower surface to facilitate securely applying the pad 224 over the window 216.

Figure 8:
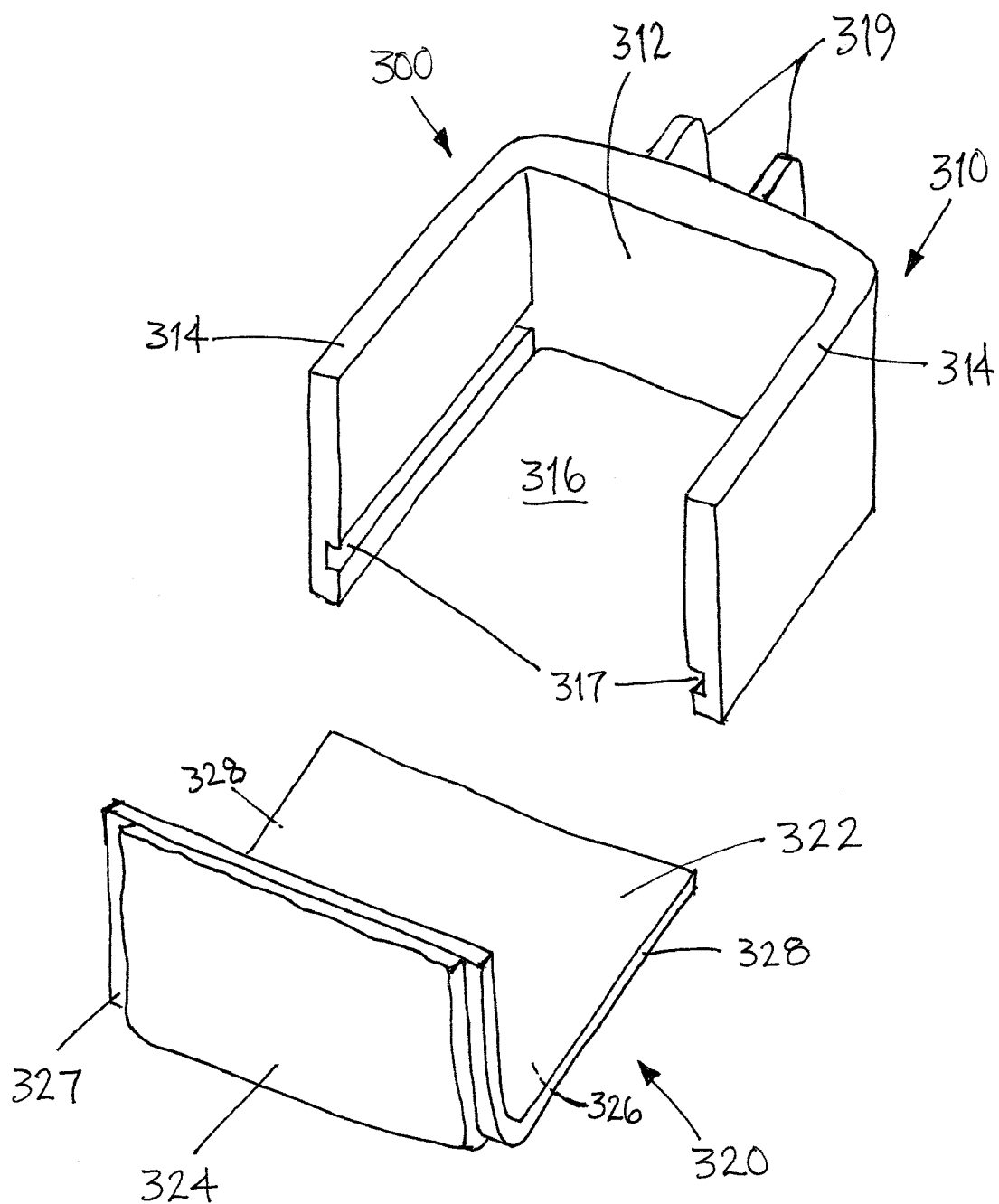
FIG. 8 is a perspective view of another embodiment of a compression device that includes a frame similar to a compression paddle, but with an open window, and a cushioning element connectable to the frame across the window.
Figure 10:
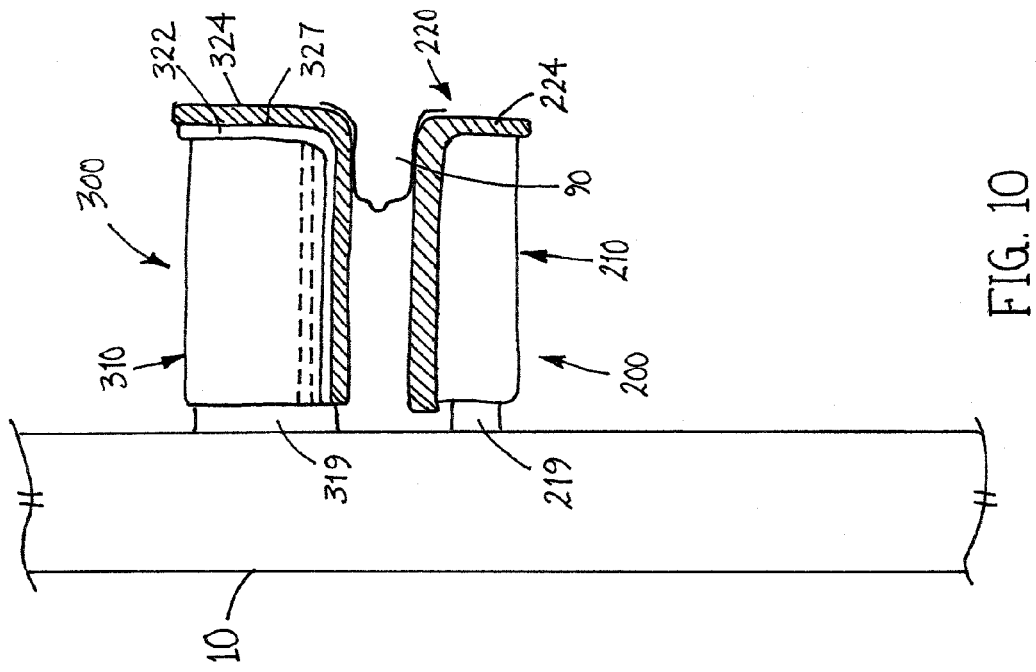
FIG. 10 is a cross-section of a mammography unit showing a method for obtaining a mammogram of a breast.
Figure 9:
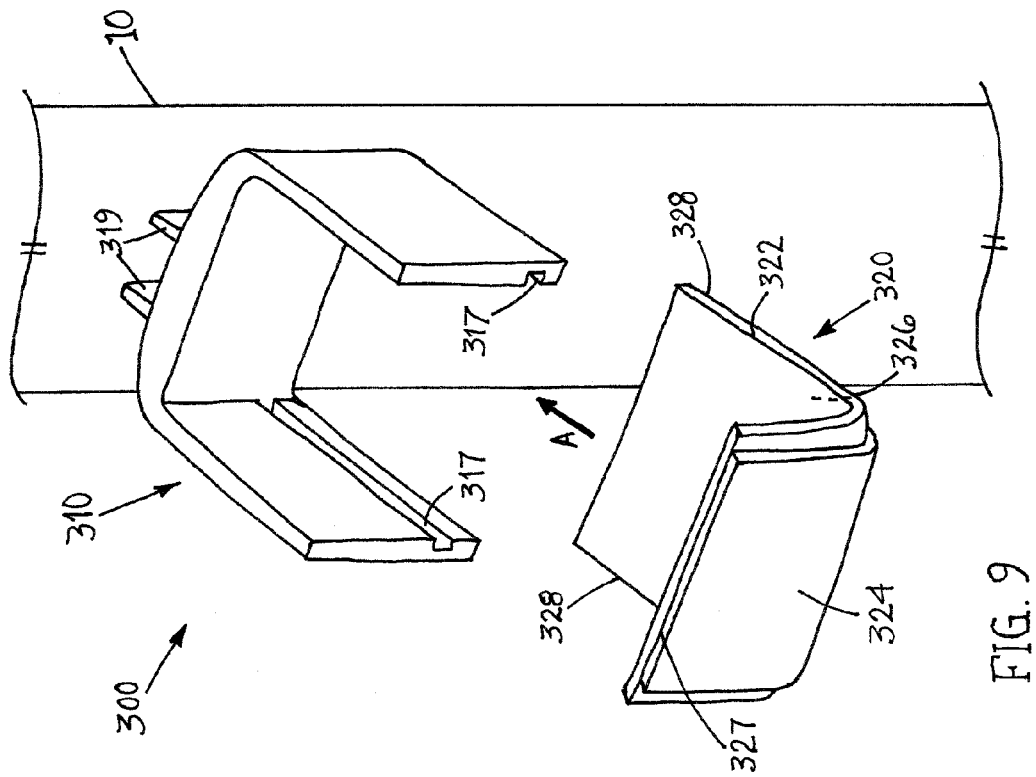
FIG. 9 is a perspective view of the compression device of FIG. 8 being attached to a mammography unit.

Turning to FIGS. 8-10, yet another embodiment of a cushioning device 300 is shown that includes a frame 310 and a pad device 320. The frame 310 generally includes a back panel 312 and a pair of side panels 314 extending from the back panel 312, thereby at least partially defining a window or opening 316. Thus, the frame 310 may generally define a "fork" shape surrounding the window 316. The side panels 314 may include slots 317 along lower edges of the side panels 314 or other connectors (not shown) for connecting or otherwise stabilizing the pad device 320 relative to the frame 310.

The pad device 320 includes a backing member 322 and a pad 324, similar to the previous embodiments. As shown, the backing member 322 includes a first or lower surface 326 (shown in FIG. 10) and a second or front surface 327 extending transversely from the first surface 326. The pad 324 may be attached to the backing member 322, e.g., such that the pad substantially covers or otherwise extends onto the first and second surfaces 326, 327, similar to the previous embodiments.

The backing member 322 includes side edges 328 (i.e., without the pad 324 thereon) that may be slidably received in the slots 317 in the frame 310. In addition or alternatively, the backing member 322 may include one or more other connectors (not shown), e.g., on or along the side edges 328, for securing the pad device 320 to the frame 310. For example, the frame 310 may include one or more alignment pins or other posts (not shown), and the pad device 320 may include corresponding holes that receive the posts. In other examples, the backing member 322 and frame 310 may include cooperating hook and loop fasteners, mating snaps, and the like, similar to the other embodiments herein.

Although the backing member 322 is shown including multiple contact surfaces, it will be appreciated that, in an alternative embodiment, a single surface backing member (not shown) may be provided that may be connected to the frame 310. In this alternative, the pad device may extend across the window 316 without extending substantially out of the plane of the window 316.

Turning to FIGS. 9 and 10, the compression device 300 may be attached to a mammography unit 10 or other x-ray device before conducting a mammography procedure. The mammography unit 10 may include one or more connectors (not shown) for connecting the compression device 300 to the mammography unit 10, e.g., instead of a conventional compression paddle. For example, the frame 310 may include a mount 319 that may be engaged or coupled with an interchange assembly (not shown) on the mammography unit 10. The frame 310 may remain on the mammography unit for an extended period of time, e.g., such that frame 310 is reused while obtaining x-rays from multiple patients.

The pad device 320 may be connected to the frame 310, e.g., by aligning the side edges 328 with the slots 317 and sliding the pad device 320 in direction "A" into and across the window 316 defined by the frame 310. For example, the pad device 320 may be advanced until the window 316 is completely covered by the pad device 320 and/or the front surface 327 contacts the side panels 314. Optionally, the pad device 320 and/or frame 310 may include detents, latches, or other locking mechanisms that engage when the pad device 320 is properly seated in the frame 310.

With the pad device 320 connected to the frame 310, the mammography unit 10 may be used to obtain x-rays from one or more patients. Optionally, as shown in FIG. 10, if desired, a compression device 200 may also be installed on the mammography unit 10. Similar to the procedure just described, a frame 210, such as shown in FIG. 7, may be attached to a stationary mating connector or mount (not shown) on the mammography unit 10. A pad device 220, such as that shown in FIG. 7, may be connected to the frame 210.

Although two compression devices 200, 300 are shown in FIG. 10, it will be appreciated that either of the compression devices 200, 300 may be replaced with a conventional compression device. For example, compression device 300 may be used with a conventional bucky, or compression device 200 may be used with a conventional compression paddle.

With one or both compression devices 200, 300 attached to the mammography unit 10, the mammography unit 10 may be used to complete one or more mammography procedures. For example, as shown in FIG. 10, a breast 90 may be disposed between the compression devices 200, 300, and one or more x-ray cassettes (not shown) may be inserted into the compression device 200 to obtain one or more mammograms of the breast 90.

Upon obtaining a desired number of mammograms for a particular patient, the pad device 220 and/or pad device 320 may be removed and replaced with a new pad device for the next patient. Alternatively, if removable covers are provided on one or both pad devices 220, 320, a cover may be removed to expose a clean cover for the next patient, as described above.

Returning to FIG. 9, an exemplary mammography procedure will now be described in more detail using the compression device 300 of FIG. 8. With the frame 310 attached to the mammography unit 10, the window 316 of the frame 310 is disposed within or around an x-ray field of the mammography unit 10. Consequently, when the pad device 320 is connected to the frame 310, the first surface 326 of the pad device 320 is also disposed within the x-ray field. Any x-rays passing along the x-ray field must pass through the first surface 326 of the backing member 322 and the pad 324. However, because the materials of the pad device 320, i.e., the backing member 322 and pad 324 are radiolucent, the mammograms obtained may not be substantially compromised by the presence of the pad device 320.

With a breast compressed between the compression device 300 and a bucky (not shown), the mammography unit 10 may automatically complete one or more tests, e.g., to determine an appropriate dosage of x-rays to obtain an effective mammogram (auto-exposure mode). With additional reference to FIG. 1, an x-ray source 16 of the mammography unit 10 may emit one or more doses of x-rays towards the bucky 20, i.e., through the compression device 300 and the patient's breast.

A receptor (not shown) in or adjacent the bucky 20 may detect the intensity of the x-rays passing completely between the x-ray source 16 and the receptor, e.g., through the compression device 300, the patient's breast, and the bucky 20. Because all materials absorb at least some x-rays the mammography unit 10 or an operator may determine that the intensity detected by the receptor is too low, and the dosage emitted by the x-ray source 16 may be increased.

For example, during a procedure using a conventional compression paddle and bucky, i.e., without any pad or cushioning element, a dosage of about seventy milliAmpere seconds (mAs) may be appropriate for a given thickness of breast tissue and other conditions.

If a gel pad is incorporated into one of the compression paddle and bucky, the dosage may need to be increased substantially, e.g., to about three hundred mAs. This may be due to the additional mass of the gel material as compared to the polycarbonate wall of the compression paddle or a foam pad of comparable thickness. For a mammography unit that automatically calibrates the dosage required given the attenuation of the x-ray path, the mammography unit may automatically increase the dosage when a gel pad is detected.

Because of the relatively higher dosage required, it may be desirable to provide a gel pad only on the compression paddle, i.e., above the breast. In this configuration, although a higher dosage is emitted by the x-ray source 16, the breast may be exposed to a much lower dosage, e.g., similar to procedures without the gel pad, because the gel pad absorbs the additional x-ray energy emitted. Thus, patient safety may not be substantially compromised even under a relatively higher dosage of x-rays.

Another advantage of providing a gel pad on the compression paddle, e.g., similar to the compression device 300 shown in FIGS. 8-10 is that the pad device 320 may be substantially transparent, allowing an operator to visually monitor the breast being compressed. For example, conventional compression paddles (without a cushioning element) may be formed from substantially transparent material. Thus, during a mammography procedure, the operator may visually observe the breast being compressed through the compression paddle to confirm proper orientation.

If a foam pad is applied to such a compression paddle (or provided on the compression device 300, the ability to visually monitor the breast may be compromised. Some foams may be at least partially translucent, at least allowing the general positioning of the underlying breast to be monitored. However, it may be more desirable to provide a pad device 320 in which both the backing material 322 and the pad 324 are substantially transparent. Gel materials are available that are both substantially transparent and radiolucent, thereby providing comfort to the patient while still allowing the operator to visually monitor the breast.

Figure 11:
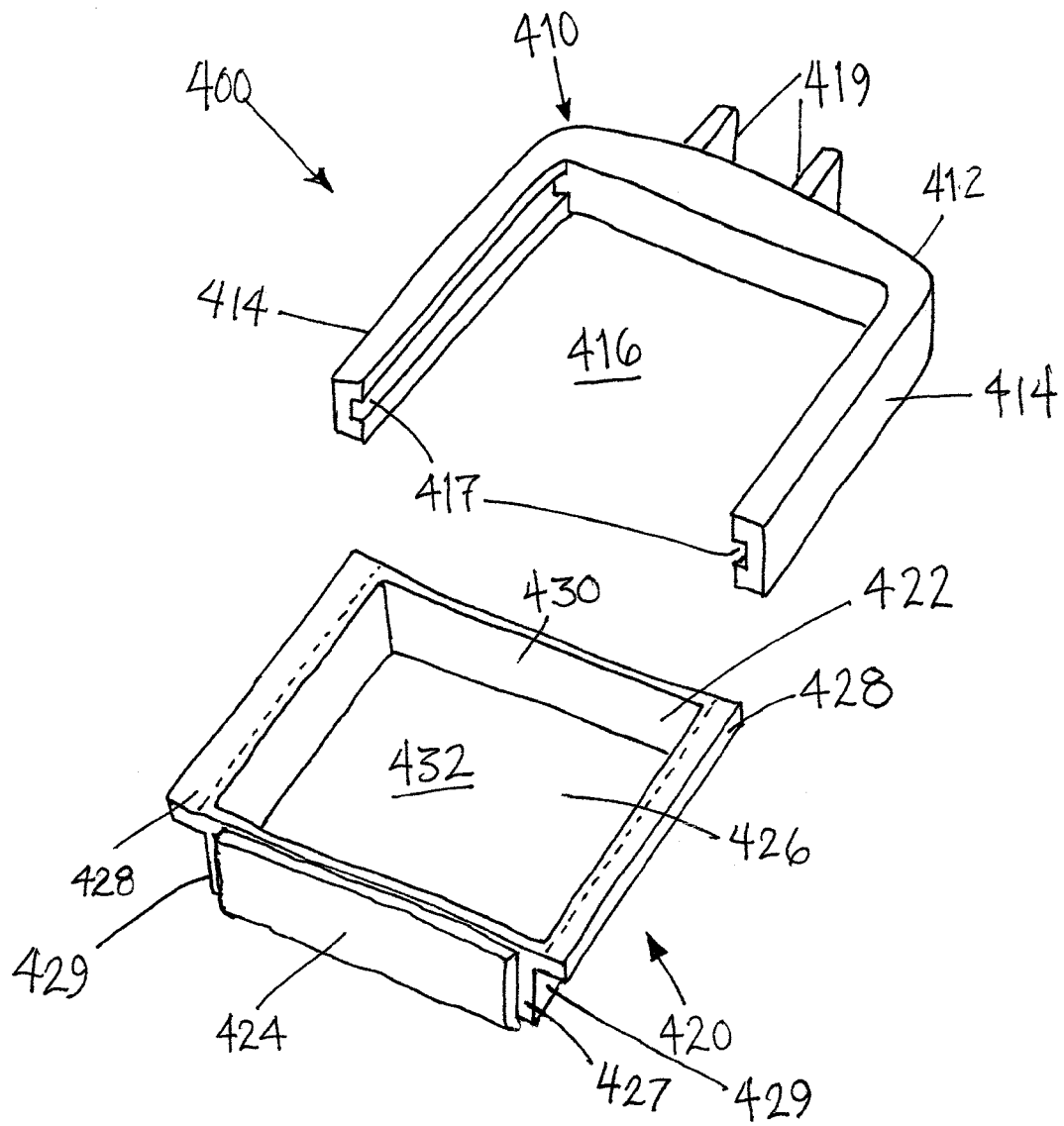
FIG. 11 is a perspective view of another embodiment of a compression device that includes a frame similar to a compression paddle, but with an open window, and a cushioning element connectable to the frame across the window.

Turning to FIG. 11, yet another embodiment of a compression device 400 is shown that includes a frame 410 and a pad device 420, which may be constructed using similar materials and methods to the embodiments described above. Unlike the previous embodiment shown in FIG. 8, the frame 410 may be a relatively flat "fork-like" member including a back panel 412 and side panels 414 that do not have substantial sidewalls. Slots 417 may be provided in the side panels 414 for slidably receiving portions of the pad device 420 therein.

The pad device 420 includes a substantially rigid paddle 422 including a lower surface 426, and a plurality of panels, e.g., a front panel 427, side panels 429, and a back panel 430, thereby defining a cavity 432. Tongues 428 may extend outwardly and/or laterally from the side panels 429 having a width and/or thickness corresponding to the slots 417. The pad device 420 also includes a pad 424 that extends onto the bottom of the lower surface 426 and, optionally, onto the front surface of the front panel 427, similar to the previous embodiments.

The compression device 400 may be used similar to the previous embodiments. For example, the frame 410 may be attached to a mammography unit (not shown), e.g., using mount 419. The pad device 420 may be connected to the frame 410 by aligning the tongues 428 with the slots 417 and sliding the pad device 420 across the window 416 of the frame 410. In this configuration, the pad device 420 may be disposed below the frame 410, with the panels providing smooth contact surfaces to enhance patient comfort. The lower surface 426 may be used to compress a breast or other tissue structure (not shown), with the pad 424 providing comfort while one or more mammograms or other x-rays are obtained, as described above.

After the procedure, the pad device 420 may be removed and replaced with a new and/or clean pad device for the next patient. Alternatively, the pad 424 may include one or more removable covers (not shown) that may be removed after each patient. Once all of the covers are depleted, the pad device 420 may be discarded.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

We claim:

1. A cushioning device for a compression plate of an x-ray device, comprising:
   a substantially rigid base comprising a first substantially transparent planar surface, the substantially rigid base being connectable along opposite side edges of the first surface to a compression plate such that the first surface is disposed within an x-ray field of the x-ray device; and
   a substantially uniform gel pad substantially permanently attached to the first surface, the gel pad being radiolucent such that the gel pad produces no significant visual artifacts on an x-ray image and being substantially transparent to allow a breast to be visually monitored through the pad and the first surface of the substantially rigid base.

2. The cushioning device of claim 1, wherein the base comprises a second surface extending transversely from the first surface, and wherein the pad extends onto the second surface.

3. The cushioning device of claim 1, wherein the base comprises one or more connectors along the side edges for connecting the cushioning device to a compression plate of an x-ray device.

4. The cushioning device of claim 3, wherein the base has a generally "L" shaped cross-section.

5. The cushioning device of claim 1, further comprising a relatively thin, radiolucent and substantially transparent film on the pad.

6. The cushioning device of claim 5, wherein the film is removably secured to the pad.

7. The cushioning device of claim 1, further comprising a plurality of relatively thin, radiolucent and substantially transparent films removable successively from the pad.

8. A device for cushioning a compression plate of an x-ray device, the compression plate comprising a primary contact surface within an x-ray field of the x- ray device, comprising:
   a frame mountable to a compression device, the frame comprising a back panel and a pair of side panels extending from the back panel and spaced apart from one another, thereby at least partially defining an open window between the side panels lying in the x-ray field when mounted to the compression device; and
   a radiolucent pad removably mounted to the frame and extending across the open window between the side panels.

9. The device of claim 8, wherein the pad comprises clear material.

10. The device of claim 8, wherein the pad comprises gel.

11. The device of claim 8, further comprising a thin, radiolucent film on the pad.

12. The device of claim 11, wherein the film comprises a removable cover.

13. The device of claim 8, further comprising a plurality of disposable covers on the pad.

14. An apparatus for an x-ray device, comprising:
a frame comprising a back panel including a connector mountable to the x-ray device, the frame comprising a pair of side panels extending from the back panel and spaced apart from one another to at least partially define an opening between the side panels disposed within an x-ray field of the x-ray device when the frame is mounted to the x-ray device; and
a radiolucent compressible member removably connectable to the side panels of the frame across the opening for providing a compression surface within the x-ray field.

15. The apparatus of claim 14, wherein the compressible member comprises a substantially rigid backing member and a radiolucent pad on the backing member.

16. The apparatus of claim 15, wherein the radiolucent pad comprises gel.

17. The apparatus of claim 15, wherein the backing member and the pad comprise an integral unit.

18. The apparatus of claim 15, wherein the pad is removably attached to the backing member.

19. The apparatus of claim 14, further comprising one or more connectors on one or both of the side panels of the frame and the compressible member for connecting the compressible member to the side panels of the frame.

20. The apparatus of claim 19, wherein the one or more connectors comprise a tongue and groove connector.

21. The apparatus of claim 14, wherein the frame comprises a lower panel extending between the side panels, thereby at least partially defining a cavity for receiving an x-ray cassette below the compressible member.

22. The apparatus of claim 21, wherein at least one of the side panels comprises a slot communicating with the cavity for at least one of inserting an x-ray cassette into the cavity and removing an x-ray cassette from the cavity.

23. The apparatus of claim 14, wherein the compressible member further comprises a front surface extending transversely relative to the compression surface within the x-ray field.

24. The apparatus of claim 23, wherein the compressible member comprises a gel pad on the compression surface within the x-ray field and on the front surface.

25. The apparatus of claim 14, wherein the compressible member comprises clear material.

26. The apparatus of claim 14, further comprising a thin, radiolucent film on the compressible member.

27. The apparatus of claim 26, wherein the film is removably secured to the compressible member.

28. The apparatus of claim 14, further comprising a plurality of removable covers on the compressible member.

29. A cushioning device for a compression plate of an x-ray device, comprising:
a substantially rigid base comprising a substantially planar, substantially transparent first surface and a second surface extending transversely relative to the first surface, the substantially rigid base being connectable along side edges of the first surface across a window of a compression plate such that the first surface is disposed within an x-ray field of the x-ray device; and
a radiolucent cushioning element substantially permanently attached to the first and second surfaces, the cushioning element being substantially transparent to allow a breast to be visually monitored through the cushioning element and the first surface of the base.

30. The device of claim 29, wherein the base comprises one or more connectors for connecting the base to a compression plate of an x-ray device.

31. The device of claim 29, wherein the cushioning element comprises gel.

32. The device of claim 29, further comprising a thin, radiolucent film on the cushioning element.

33. A method for performing mammography using a mammography unit including a compression plate, the compression plate comprising a back panel and a pair of side panels extending from the back panel and spaced apart from one another to at least partially define an open window between the side panels within an x-ray field of the mammography unit, the method comprising:
connecting a radiolucent cushioning element to the compression plate across the window;
compressing a breast against the cushioning element, the cushioning element deforming under forces applied during compression to provide comfort; and
obtaining a mammogram of the compressed breast.

34. The method of claim 33, further comprising removing the cushioning element from the compression plate.

35. The method of claim 33, wherein the cushioning element is connected to the side panels.

36. The method of claim 33, wherein the compression plate comprises a lower panel extending between the side panels, thereby at least partially defining a cavity for receiving an x-ray cassette.

37. The method of claim 36, wherein at least one the side wall comprises an opening communicating with the cavity for at least one of inserting an x-ray cassette into the cavity and removing an x-ray cassette from the cavity.

38. The method of claim 33, wherein the cushioning element comprises a substantially rigid base and a pad on the base, and wherein the cushioning element is connected to the compression plate by engaging the base with one or more connectors on the compression plate.

39. The method of claim 38, wherein the base comprises side edges, and wherein the one or more connectors comprise slots in the compression plate for receiving the side edges of the base.

40. A method for performing mammography, comprising:
connecting a frame to a mammography unit, the frame including a back panel and a pair of side panels extending from the back panel and spaced apart from one another to at least partially define an opening extending between the side panels across an x-ray field of the mammography unit;
connecting a substantially transparent cushioning element to the frame such that the pad device extends across the opening to provide a mammography paddle;
compressing a breast using the mammography paddle;
visually monitoring the breast through the cushioning element; and
obtaining a mammogram of the compressed breast.

41. The method of claim 40, wherein the cushioning element comprises a substantially transparent backing member comprising a patient contact surface and a substantially transparent gel pad on the patient contact surface.

42. The method of claim 41, further comprising:
emitting x-rays through the mammography paddle; and
adjusting a dosage of x-rays emitted when the mammogram is obtained to account for attenuation of the gel pad.

43. The method of claim 40, further comprising removing the cushioning element from the frame after obtaining the mammogram.

44. The method of claim 40, wherein the breast is visually monitored through the cushioning element during positioning.

45. The device of claim 8, wherein the radiolucent pad comprises:
- a substantially rigid base comprising a first planar surface, the substantially rigid base being connectable along opposite side edges of the first surface to the side panels of the frame such that the first surface is disposed within an x-ray field of the x-ray device; and
- a gel pad substantially permanently attached to the first surface, the gel pad being substantially radiolucent such that the gel pad produces no significant visual artifacts on an x-ray image.

46. The device of claim 45, wherein the base is substantially transparent and the gel pad is substantially transparent to allow a breast to be visually monitored through the pad and the first surface of the base.

* * * * *